United States Patent [19]

Szóke et al.

[11] 4,368,328
[45] Jan. 11, 1983

[54] PROCESS FOR PREPARING ALKYLTHIOBENZIMIDAZOLES

[75] Inventors: Sándor Szóke, Budapest; György Lugosi, Felső-God; Mária Bakonyi, Budapest; Jenó Ghyczy, Budapest; Gyorgy Csermely, Budapest, all of Hungary

[73] Assignee: Chinoin Gyogyszer es Vegyeszeti Termekek Gyara Rt., Budapest, Hungary

[21] Appl. No.: 212,628

[22] Filed: Dec. 3, 1980

[30] Foreign Application Priority Data

Apr. 12, 1979 [HU] Hungary ............................... CI 1993

[51] Int. Cl.³ .................. C07D 235/04; C07D 233/66
[52] U.S. Cl. .................................... 548/306; 548/325; 548/337
[58] Field of Search ...................... 548/337, 306, 325

[56] References Cited

U.S. PATENT DOCUMENTS 2,654,762 10/1953 Huebner et al. ..................... 548/337
3,996,369 12/1976 Loewe et al. ....................... 548/306
4,259,344 3/1981 Gonezi et al. ....................... 548/337

OTHER PUBLICATIONS

Noller, Textbook of Organic Chemistry, W. B. Saunders Co., Philadelphia, Pa., 1958, p. 357.
Reid, Organic Chemistry of Bivalent Sulfur, Chem. Publishing Co., Inc., 212 5th Ave., New York, 1958, p. 36.
Sayapin et al., Chem. Abs., 73, 45409p (1970).
Holan et al., J. Chem. Soc., 1967, p. 20.

Primary Examiner—Henry R. Jiles
Assistant Examiner—Robert C. Whittenbaugh
Attorney, Agent, or Firm—Karl F. Ross

[57] ABSTRACT

The invention concerns a new process for the preparation of biologically active 2-[(alkoxycarbonyl)amino]-5-(alkylthio)-1H-benzimidazoles of the general formula (V)

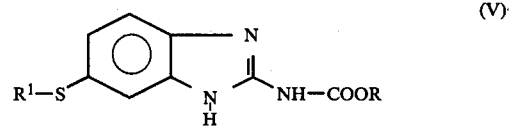

wherein
R and R¹ independently stand for alkyl having 1 to 3 carbon atoms.

6 Claims, No Drawings

PROCESS FOR PREPARING ALKYLTHIOBENZIMIDAZOLES

The present invention relates to a new process for the preparation of alkylthiobenz-imidazoles. More particularly, this invention concerns a new process for preparing biologically active 2-[(alkoxycarbonyl)amino]-5-(alkylthio)-1H-benzimidazoles of the formula (V)

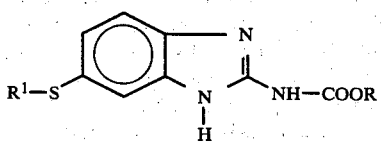

wherein

R and $R^1$ independently stand for alkyl having 1 to 3 carbon atoms.

The compounds of the formula (V) are conventionally prepared from the corresponding 4-alkylthio-phenylenediamines by reactants capable of forming an imidazole ring. Suitable reactants include the corresponding carboalkoxycyane amides, directly yielding the desired end products, and bromocyane, which results in the formation of a 2-amino-5-alkylthiobenzimidazole, which is then reacted with an alkyl chloroformate to give the desired end product. A detailed description of these processes is be found in the U.S. Pat. No. 3,956,499 and in the Hungarian Pat. No. 172,538. These patents disclose the preparation of 2-[(methoxycarbonyl)amino]-5-(propylthio)-1H-benzimidazole, a prominent representative of the compounds of the formula (V), having valuable anthelmintic properties.

The most important disadvantages of the processes known in the art consist in the fact that 4-alkylthio-1,2-phenylenediamines are rather expensive and difficult to prepare, some of the reactants employed are toxic and have an unpleasant odor, and a dangerous and expensive catalytic hydrogenation step is involved.

The present invention relates to a new process for the preparation of 2-[(alkoxycarbonyl)amino]-5-(alkylthio)-1H-benzimidazoles of the formula (V)—wherein R and $R^1$ are as hereinbefore defined—which is devoid of the above disadvantages. According to the invention compounds of the formula (V) are prepared by reacting (1H-benzimidazol-2-yl)carbamic acid alkyl esters of the formula (I)

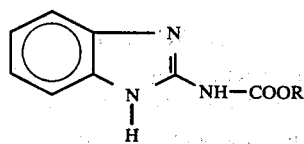

wherein R has the same meaning as defined above, with
(a) chlorosulfonic acid, or
(b) oleum, to yield a corresponding 2-[(alkoxycarbonyl)amino]-1H-benzimidazole-5-sulfonic acid of the formula (II)

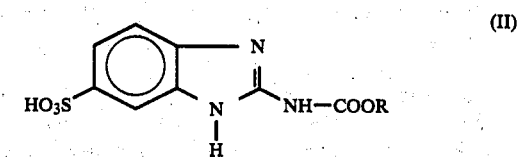

wherein R is as defined above, and subsequently with a chlorinating agent, reducing a 2-[(alkoxycarbonyl)amino]-1H-benzimidazole-5-sulfonic acid chloride of the formula (III)

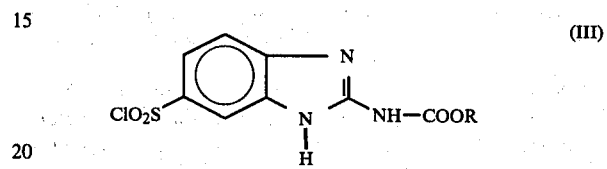

where R is as defined above, obtained, by variant (a) or (b) and finally reacting a 2-[(alkoxycarbonyl)amino]-1H-benzimidazole-5-thiol of the formula (IV)

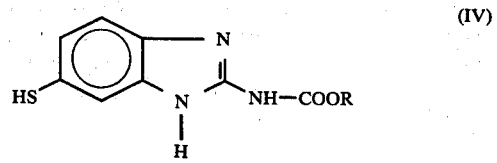

wherein R is as defined above, obtained with an alkyl halide of the formula

$R^1$—Hal     (VI)

wherein $R^1$ is as hereinbefore defined and Hal represents halogen.

The term "alkyl" alone or in alkyl-containing groups is used to refer to straight or branched chained hydrocarbon groups having 1 to 3 carbon atoms, i.e. methyl, ethyl, n- and isopropyl groups.

The term "halogen" stands for fluorine, chlorine, bromine or iodine.

As chlorinating agents phosphorus oxychloride, phosphorus pentachloride or pyrocatechyl phosphorus trichloride can for example be used.

The reduction of the compounds of the formula (III) is preferably carried out in an aqueous acidic medium, with metals or metal salts.

2-[(alkoxycarbonyl)amino]-1H-benzimidazole-5-sulfonic acids of the formula (II) and salts thereof, 2-[(alkoxycarbonyl)amino]-1H-benzimidazole-5-sulfonic acid chlorides of the formula (III) and salts thereof, and 2-[(alkoxycarbonyl)amino]-1H-benzimidazole-5-thiols of the formula (IV) and salts thereof, obtained as intermediates in the synthesis according to the invention are new compounds.

2-[(Alkoxycarbonyl)amino]-1H-benzimidazole-5-sulfonic acids of the formula (II) are obtained in the form of white crystals, by reacting a corresponding (1H-benzimidazol-2-yl)-carbamic acid alkyl ester of the formula (I) with a 20% oleum at 30° to 60° C. and pouring the reaction mixture into ether.

2-[(Alkoxycarbonyl)amino]-1H-benzimidazole-5-sulfonic acid chlorides of the formula (III) can be prepared by (a) reacting a corresponding compound of the formula (I) with chlorosulfonic acid at a temperature between 15° C. and 40° C. and subsequently pouring the reaction mixture into absolute alcohol or on ice, when the product is obtained as a hydrochloride, or into a mixture of ether and ethyl acetate, when a corresponding sulfuric acid addition salt is obtained, or (b) converting a compound of the formula (II) into the sodium salt thereof with sodium hydroxide in a methanolic medium, melting the salt obtained with phosphorus pentachloride at 110° C. and finally pouring the reaction mixture on ice.

When a 2-[(alkoxycarbonyl)amino]-1H-benzimidazole-5-sulfonic acid chloride of the formula (III) is reduced with a metal or metal salt in an aqueous acidic medium, at 0° to 100° C., 2-[(alkoxycarbonyl)amino]-1H-benzimidazole-5-thiol of the formula (IV) is obtained, which precipitates as a white crystalline substance.

The compound of the formula (IV) obtained is then dissolved in dimethyl formamide, the pH is adjusted to 8 to 9 with an aqueous alkaline solution, it is reacted with an alkyl halide, preferably bromide at room temperature and the solution is diluted with water to yield 2-[(alkoxycarbonyl)amino]-5-alkylthio-1H-benzimidazole of the formula (V), which can easily be filtered off.

An important advantage of the process according to the invention over the methods known in the art consists in the fact that compounds of the general formula (I) used as starting materials are cheap industrial products, from which end products of the formula (V) can be prepared by simple technological steps, using readily available and cheap reactants.

Further details of the invention are to be found in the following Examples, which are not intended to limit the scope of the invention in any way.

EXAMPLE 1

2-[(Methoxycarbonyl)amino]-1H-benzimidazole-5-sulfonic acid

Into a 250-ml. four-neck, round-bottomed flask, equipped with a stirrer, thermometer and a sulfuric acid bubbler 120 ml. of a 20% oleum are weighed, whereupon 38.4 g. (0.2 moles) of (1H-benzimidazol-2-yl)-carbamic acid methyl ester are added dropwise, at 30° to 40° C., under a slight cooling with ice water, in 15 to 20 minutes. The temperature is then raised to 55° to 60° C. and the reaction mixture is stirred for two hours.

1200 ml. of ethyl ether are cooled to −10° C. with salted ice and the above reaction mixture is poured into the cool ether, at a rate, which ensures that the temperature does not exceed 0° C.

The title product precipitates as a white, crystalline substance, which is then filtered off, washed with cooled ether and subsequently with 100 ml. of cooled absolute ethanol and dried. Weight: 43.5 g. (theoretical: 54.26 g.). Yield: 80%

Analysis:
found: C=39.2%, H=3.5%, N=15.1%, S=12.1%
calculated: C=39.84%, H=3.34%, N=15.49%, S=11.8%

EXAMPLE 2

2-[(Methoxycarbonyl)amino]-1H-benzimidazole-5-sulfonic acid chloride. HCl

Into a 500-ml. flask, equipped with a stirrer 81.3 g. (0.3 moles) of 2-[(methoxycarbonyl)amino]-1H-benzimidazole-5-sulfonic acid and 300 ml. of methanol are weighed. The pH of the reaction mixture is adjusted to 7.5 with dropwise addition of a 40% aqueous sodium hydroxide solution at room temperature. The starting compound is dissolved in the mixture whereupon precipitation of 2-[(methoxycrbonyl)amino]-1H-benzimidazole-5-sulfonic acid sodium salt can be observed. After stirring for one hour, the mixture is filtered, and the precipitate is washed with a small portion of methanol and is subsequently dried. Weight: 90 g.

The dry sulfonic acid salt is then melted with 130 g. (0.625 moles) of phosphorus pentachloride at 110° C. and is stirred at the same temperature for an additional two hours.

The mixture is poured onto 400 g. of broken ice, is washed with ice water and subsequently with 100 ml. of absolute ethanol of −10° C., and is dried. 82 g. of the title compound are obtained (theoretical: 97.86 g.).

Yield: 84%

Analysis:
found: C=32.9%, H=3.0%, Cl=21.6%, N=13.0%, S=9.75%. calculated: C=33.14%, H=2.78%, Cl=21.74%, N=12.88%, S=9.83%.

EXAMPLE 3

2-[(Methoxycarbonyl)amino]-1H-benzimidazole-5-sulfonic acid chloride. HCl

Into a 250-ml. four-necked, round-bottomed flask, equipped with a stirrer, thermometer and a sulfuric acid bubbler 100 ml. (178.7 g, 1.53 moles) of chlorosulfonic acid are weighed, followed by the addition of 38.4 g. (0.2 moles) of (1H-benzimidazol-2-yl)-carbamic acid methyl ester at 15° to 20° C., under slight cooling with ice water, in about 30 minutes. The reaction mixture is then heated up to 40° C. and is stirred at this temperature for 2.5 hours. The reaction mixture is poured into 1000 ml. of absolute ethanol, and cooled to −10° C. at a rate, which ensures that the temperature does not exceed 0° C. An intensive cooling with salted ice is required.

The precipitated white crystalline product is filtered off, washed with 100 ml. of cooled absolute ethanol and dried. Weight: 60.6 g. (theoretical: 62.2 g.).

Yield: 93%.

Melting point: 250° C.

Analysis:
found: C=32.94%, H=3.02%, Cl=21.64%, N=12.91%, S=9.81%. calculated: C=33.14%, H=2.78%, Cl=21.74%, N=12.88%, S=9.83%.

EXAMPLE 4

2-[(Methoxycarbonyl)amino]-1H-benzimidazole-5-sulfonic acid chloride. HCl

The procedure described in Example 3 is followed, except that the product is isolated from the reaction mixture as follows:

The reaction mixture containing chlorosulfonic acid is poured onto 800 g. of broken ice. The precipitated product is filtered off, washed with a small portion of ice water and subsequently with 100 ml. of absolute ethanol cooled to −10° C., and is dried. 52.1 g. of the title compound are obtained (theoretical: 65.2 g.).

Yield: 80%

The acid chloride isolated from water is preferably used without drying, since during drying decomposition takes place.

EXAMPLE 5

2-[(Methoxycarbonyl)amino]-1H-benzimidazole-5-sulfonic acid chloride.$H_2SO_4$

Into a 200-ml. four-necked, round-bottomed flask, equipped with a stirred, thermometer and a sulfuric acid bubbler 100 ml. (175.7 g.; 1.53 moles) of chlorosulfonic acid are weighed, followed by the addition of 38.4 g. (0.2 moles) of (1H-benzimidazol-2-yl)-carbamic acid methyl ester at 15° to 20° C., under slight cooling with ice water, in about 30 minutes. The reaction mixture is heated up to 40° C., is stirred at this temperature for 2.5 hours, whereupon it is poured into a mixture of 1000 ml. of ethyl ether and 300 ml. of ethyl acetate cooled to −10° C. at a rate, which ensures that the temperature does not exceed 0° C.

The precipitated white crystalline product is filtered off, washed with 200 ml. of cooled ether and dried in a vacuum desiccator. (The dried product is not hygroscopic any more.) 64.40 g. of the title compound are obtained (theoretical: 77.4 g.).

Yield: 83.2%, melting point: 142° to 145° C. (decomp.)

Analysis:
found: C=27.52%, H=2.8%, Cl=9.18%, N=10.12%, S=16.45%, calculated: C=27.87%, H=2.6%, Cl=9.14%, N=10.83%, S=16.54%.

EXAMPLE 6

2-[(Methoxycarbonyl)amino]-5-propylthio-1H-benzimidazole

Into 110 ml. of a 40% aqueous sulfuric acid solution 20 g. of Zn powder are added at 0° C., followed by the addition of 10.8 g. (0.033 moles) of 2-(methoxycarbonyl)amino-1H-benzimidazole-5-sulfonic acid chloride hydrochloride. The reaction mixture is then stirred at 0° C. for two hours. Thereafter it is heated up to 80° to 90° C. and stirred at this temperature for one hour. 2-[(Methoxycarbonyl)amino]-1H-benzimidazole-5-thiol precipitates as a white crystalline substance. It is cooled to room temperature, filtered off and washed with a small portion of ice water. The precipitate is dissolved in a five-times amount of dimethyl formamide related to its weight. The undissolved zinc is filtered off and washed with dimethyl formamide. The pH of the reaction mixture is adjusted to 8 to 9 with a 40% aqueous sodium hydroxide solution, 6 ml. of n-propyl bromide are added, while the temperature is kept at 25° to 30° C. by cooling with ice water. The mixture is stirred for half an hour and is subsequently allowed to stand for 48 hours. The precipitate is filtered off, washed with water and then with acetone, and is dried. 5.50 g. (62.8% of theoretical) of the title compound are obtained, melting at 208° to 210° C. after recrystallization from chloroform (decomp.).

Analysis:
found: C=54.36%, H=5.64%, H=16.00%, S=11.92%. calculated: C=54.32%, H=5.70%, H=15.84%, S=12.00%.

EXAMPLE 7

2-[(Methoxycarbonyl)amino]-5-propylthio-1H-benzimidazole 10.8 g. (0.033 moles) of 2-[(Methoxycarbonyl)amino]-1H-benzimidazole-5-sulfonic acid chloride hydrochloride are suspended in 35 ml. of water, 33 g. of $SnCl_2$ are added and the mixture is stirred at 50 C. for 30 minutes. A clear solution is obtained and then the precipitation of a crystalline substance can be observed. The mixture is cooled to room temperature, filtered and the precipitate is washed with a small portion of ice water. 2-[(Methoxycarbonyl)amino]-1H-benzimidazole-5-thiol obtained is further treated as described in Example 6 to yield 5 g. of the title compound, melting at 210° C.

EXAMPLE 8

2-[(Ethoxycarbonyl)amino]-1H-benzimidazole-5-sulfonic acid chloride. HCl

Into 100 ml. (178.7 g.; 1.53 moles) of chlorosulfonic acid 41 g. (0.2 moles) of 1H-benzimidazol-2-yl)-carbamic acid ethyl ester are added at 15° to 20° C. in about 30 minutes. The reaction mixture is heated up to 40° C. and is stirred for 2.5 hours. It is then poured into absolute ethanol cooled to −10° C. The precipitated white crystalline product is filtered off, washed with ethanol and dried. 59 g. of the title compound are obtained (theoretical: 68 g.).

Analysis:
found: C=35.0%, H=3.1%, Cl=20.60%, N=12.70%, S=9.3%, calculated: C=35.3%, H=3.26%, Cl=20.84%, N=12.35%, S=9.43%.

EXAMPLE 9

2-[(Ethoxycarbonyl)amino]-5-ethylthio-1H-benzimidazole

Into 110 ml. of a 40% aqueous sulfuric acid solution 20 g. of zinc powder are added at 0° C. followed by the addition of 11.2 g. (0.033 moles) of 2-[(ethoxycarbonyl)amino]-1H-benzimidazole-5-sulfonic acid chloride hydrochloride with stirring. The reaction mixture is stirred at 0° C. for two hours. It is then heated up to 80° to 90° C. and is stirred at this temperature for one hour. 2-[(Ethoxycarbonyl)amino]-1H-benzimidazole-5-thiol precipitates as a white crystalline substance. The precipitate is dissolved in five-times of its weight of dimethyl formamide and the undissolved zinc powder is filtered off. The pH of the reaction mixture is adjusted to 8 to 9 with an aqueous sodium hydroxide solution, 5 ml. of ethyl bromide are added and the mixture is allowed to stand for 48 hours. The title compound precipitates upon dilution with water. It is then filtered off and washed with water and acetone. Weight: 4.4 g.

Analysis:
found: C=54.2%, H=5.58%, N=15.90%, S=11.85%; calculated: C=54.32%, H=5.70%, N=15.84%, S=12.08%.

EXAMPLE 10

2-[(Methoxycarbonyl)amino]-5-propylthio-1H-benzimidazole

Into 100 ml. of a 10% aqueous hydrochloric acid solution 1.5 g. of Sn powder are added at 0° to 10° C., followed by the addition of 10.8 g. (0.033 moles) of 2-[(methoxycarbonyl)amino]-1H-benzimidazol-5-sulfonic acid chloride hydrochloride. The reaction mixture is stirred at the same temperature for one hour.

Thereafter 10 g. of Fe powder are added and it is stirred at 25° to 30° C. for 6 hours. The metals are dissolved and 2-[(methoxycarbonyl)amino]-1H-benzimidazole-5-thiol precipitates. The precipitate is filtered off, dissolved in a 10% aqueous potassium hydroxide solution and is subsequently reacted with 6 ml. of n-propyl bromide at 40° to 45° C.

The precipitated title compound is filtered off, washed with water and acetone, and dried. Weight: 4 g. Melting point: 213° to 214° C. (decomp.)

EXAMPLE 11

2-[(Methoxycarbonyl)amino]-5-propylthio-1H-benzimidazole

Into 100 ml. of a 10% aqueous hydrochloric acid solution 10.8 g. (0.033 moles) of 2-[(methoxycarbonyl)amino]-1H-benzimidazole-5-sulfonic acid chloride hydrochloride and 10 g. of Fe powder are added at room temperature. The mixture is stirred at 70° to 80° C. for 5 hours, whereupon the precipitated 2-[(methoxycarbonyl)amino]-1H-benzimidazole-5-thiol is filtered off and converted into 2-[(methoxycarbonyl)amino]-5-propylthio-1H-benzimidazole as described in Example 10. The product melts at 208° to 210° C.

EXAMPLES 12

2-[(Methoxycarbonyl)amino]-1H-benzimidazole-5-thiol

Into 100 ml. of a 10% aqueous hydrochloric acid solution 6 g. of Sn powder and 10.8 g. (0.033 moles) of 2-[(methoxycarbonyl)amino]-1H-benzimidazole-5-sulfonic acid chloride hydrochloride are added at a temperature between 0° C. and 10° C. The reaction mixture is stirred below 10° C. for two hours and subsequently at 25° C. for 10 hours. The starting compound is dissolved and thereafter the title compound precipitates. Weight: 6 g. (81.5%). Melting point: 214° to 215° C. (decomp.)

Analysis:
found: C=48.22%, H=4.20%, N=18.52%, S=13.80%, calculated: C=48.60%, H=4.06%, N=18.88%, S=14.39%.

We claim:

1. A process for the preparation of a compound of the formula (V)

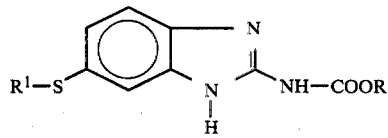

wherein
R and $R^1$ are each independently $C_1$ to $C_3$ alkyl, which comprises the steps of:
(a) sulfonating a compound of the formula (I)

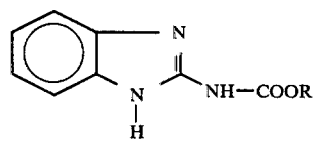

with oleum at 30° to 60° C. to form a compound of the formula (II)

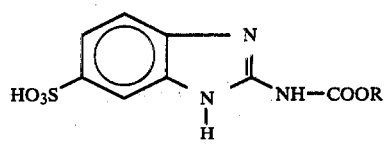

(b) converting the compound of the formula (II) into the sodium salt thereof with aqueous sodium hydroxide;
(c) chlorinating the sodium salt of the formula (II) with a chlorinating agent selected from the group consisting of phosphorus oxychloride, phosphorus pentachloride, and pyrocatechyl phosphorus trichloride to form a compound of the formula (III)

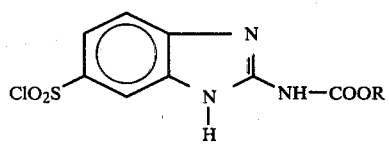

(d) reducing the compound of the formula (III) at a temperature between 0° and 100° C. with a metal or metal salt in an aqueous acidic medium to form a compound of the formula (IV)

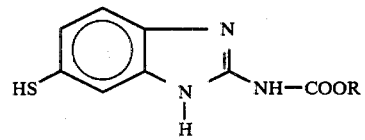

and, (e) alkylating the compound of the formula (IV) with an alkyl halide of the formula (VI)

$R^1$—Hal wherein Hal is halogen at room temperature to yield the desired product.

2. A process for the preparation of a compound of the formula (III)

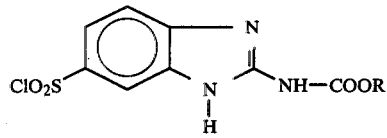

wherein R is $C_1$ to $C_3$ alkyl, which comprises the steps of chlorosulfonating a compound of the formula (I)

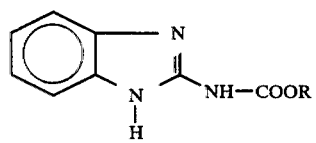

with chlorosulfonic acid at a temperature between 15° and 40° C.

3. A process for the preparation of a compound of the formula (V)

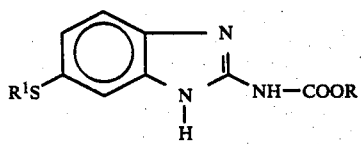

wherein
R and R¹ are each independently $C_1$ to $C_3$ alkyl,
which comprises the steps of:
(a) chlorosulfonating a compound of the formula
(I)

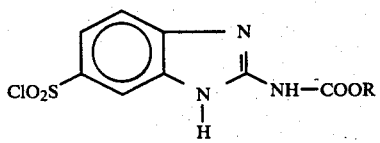

with chlorosulfonic acid at a temperature between 15° and 40° C. to form a compound of the formula (III)

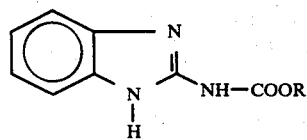

(b) reducing the compound of the formula (III) at a temperature between 0° and 100° C. with a metal or metal salt in an aqueous acidic medium to form a compound of the formula (IV)

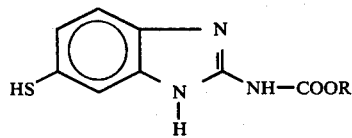

and, (c) alkylating the compound of the formula (IV) with an alkyl halide of the formula (VI)

R¹—Hal wherein Hal is halogen at room temperature to yield the desired product.

4. A compund of the formula (II)

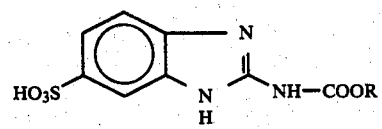

wherein R stands for an alkyl group having 1 to 3 carbon atoms, and salts thereof.

5. A compound of the formula (III)

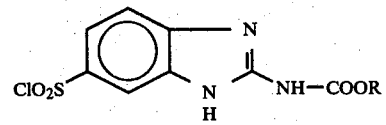

wherein R stands for an alkyl group having 1 to 3 carbon atoms, and acid addition salts thereof.

6. A process for the preparation of a compound of the formula (III)

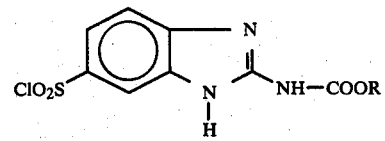

wherein R is $C_1$ to $C_3$ alkyl, which comprises the steps of
(a) sulfonating a compound of the formula (I)

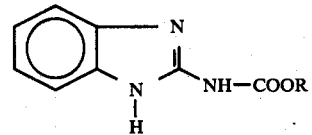

with oleum at 30° to 60° C. to form a compound of the formula (II)

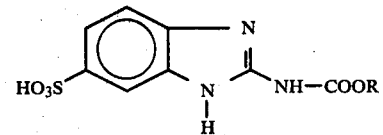

(b) converting the compound of the formula (II) into the sodium salt thereof with aqueous sodium hydroxide; and
(c) chlorinating the sodium salt of the compound of the formula (II) with a compound selected from the group consisting of phosphorus oxychloride, phosphorus pentachloride and pyrocatechyl phosphorustrichloride to yield the desired product.

* * * * *